United States Patent [19]

Bright et al.

[11] Patent Number: 5,420,327
[45] Date of Patent: May 30, 1995

[54] PROCESS FOR FORMING HYDROCARBYL BISPHOSPHATE COMPOUND

[75] Inventors: Danielle A. Bright, New City; Ronald L. Pirrelli, Hartsdale, both of N.Y.

[73] Assignee: Akzo Nobel N.V., Arnhem, Netherlands

[21] Appl. No.: 120,142

[22] Filed: Sep. 10, 1993

Related U.S. Application Data

[63] Continuation of Ser. No. 944,638, Sep. 14, 1992, abandoned.

[51] Int. Cl.$^6$ ................................................. C07F 9/12
[52] U.S. Cl. ....................................... 558/99; 558/162; 558/164
[58] Field of Search ............................. 558/99, 162

[56] References Cited

U.S. PATENT DOCUMENTS

| | | | |
|---|---|---|---|
| 2,520,090 | 8/1950 | Barrett | 260/461 |
| 2,668,174 | 2/1954 | Horback et al. | 558/99 X |
| 3,254,973 | 6/1966 | Giammana et al. | 44/69 |
| 3,812,220 | 5/1974 | Robin | 260/953 |
| 4,133,846 | 1/1979 | Albright | 260/928 |
| 4,134,876 | 1/1979 | Horner et al. | 260/45.7 |
| 4,343,732 | 8/1982 | Zama et al. | 524/114 |
| 4,724,247 | 2/1988 | Burton et al. | 558/162 X |

FOREIGN PATENT DOCUMENTS

| | | | |
|---|---|---|---|
| 509506 | 10/1992 | European Pat. Off. | C07F 9/12 |
| 63-227632 | 9/1988 | Japan | C08G 79/04 |

*Primary Examiner*—Mary C. Lee
*Assistant Examiner*—Michael G. Ambrose
*Attorney, Agent, or Firm*—Richard P. Fennelly; Louis A. Morris

[57] ABSTRACT

Hydrocarbyl bisphosphate compounds containing hindered aryl substituents in the phosphate groups can be formed by: (a) reacting a hindered phenol, e.g., xylenol, with a phosphorus oxytrihalide, e.g., phosphorus oxytrichloride, to form a reaction product mixture; and (b) combining the reaction product, without distillation of the product from the reaction product mixture, from (a) mixture with a hydrocarbyl diol, e.g., one containing a phenyl ring such as hydroquinone or resorcinol.

6 Claims, No Drawings

PROCESS FOR FORMING HYDROCARBYL BISPHOSPHATE COMPOUND

This is a continuation of application Ser. No. 07/944,638, filed Sep. 14, 1992, abandoned.

BACKGROUND OF THE INVENTION

Hydrocarbyl bisphosphate compounds of the general formula

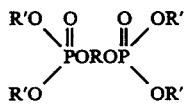

where R and R' are the same or different and are hydrocarbyl groups which are either substituted with non-interfering substituents or are unsubstituted are a known class of flame retardant additive. Some examples of groups which form the basis for such groups are alkyl(ene) and aryl(ene). Representative substituents include alkyl.

U.S. Pat. No. 4,134,876, British Patent No. 2,061,949, and Japanese Patent Publication No. 227,632/1988 which all relate to compounds of this general type teach that they may be formed by first reacting $POCl_3$ with a diol containing the group desired for R to form a product which is then reacted with an alcohol containing the desired group R'. Unfortunately, when such a reaction is performed, an undesired amount of oligomeric product is commonly formed in the first reaction of diol and $POCl_3$.

U.S. Pat. No. 3,254,973 illustrates reaction of phosphorus oxychloride and ortho-cresol to form di-o-tolyl phosphorochloridate which is then reacted with bisphenol A. No discussion is contained in this reference regarding the formation of undesired oligomeric products or of triphenyl phosphate. Also, this patent indicates that the reaction mixture from the initial reaction of phosphorus oxychloride and o-cresol is distilled through a packed column to isolate various cuts of di-o-tolyl phosphorochloridate. Those cuts distilling at 182°–187° C. were combined for later use as a reagent for reaction with bisphenol A to form the desired bisphosphate end-product. The need for distillation in the process shown in this patent has certain disadvantages. First, the presence of the distillation step makes the overall process more complicated and expensive than an analogous process not containing the need for distillation of product di-o-tolyl phosphorochloridate in view of both the presence of the step itself as well as the need for the equipment for distillation (distillation column and collection vessel). Second, since the product which is distilled is corrosive, the extra distillation equipment needed must have appropriate materials of construction which can also raise the expense of the overall process.

SUMMARY OF THE INVENTION

The present invention relates to a process for forming a hydrocarbyl bisphosphate compound containing hindered aryl substituents in the phosphate groups which comprises: (a) reacting a hindered phenol with a phosphorus oxytrihalide to form a reaction product mixture; and (b) combining the reaction product mixture from (a), without distillation of product therefrom, with a hydrocarbyl diol to form the bisphosphate. This procedure results in a lessened amount of oligomer formation in its first step as compared to the type of process known to the prior art which reacted the diol in step (a) and the alcohol (e.g., phenol) in step (b).

DETAILED DESCRIPTION OF THE INVENTION

The first step in the process of the present invention involves the use, as one reagent, of a hindered phenol of the formula

R'OH where R' is a phenyl group substituted by one or more substituents, e.g., lower alkyl group substituents such as methyl, ethyl, propyl, n-butyl, and t-butyl, at ring position(s) adjacent the hydroxy group (e.g., ortho-) in order to provide some measure of steric hindrance to the hydroxy substituent.

The type and number of substituents as well as their positions need to be appropriately coordinated to achieve the proper degree of steric hindrance so that the product, after reaction with the phosphorus oxyhalide, need not be distilled from the reactionsmixture as shown necessary by U.S. Pat. No. 3,254,973. If a single substituent is selected, the substituent needs to be more bulky than if two hindering substituents are used. For example, one which is branched (e.g., t-butyl) may need to be selected. When two hindering substituents are used, as in the case of 2,6-xylenol, the alkyl group can include such lower alkyl groups as methyl and ethyl. One particularly preferred reagent is 2,6-xylenol.

The other reagent in the first step of the process is a phosphorus oxyhalide, such as phosphorus oxychloride.

The hindered phenol and phosphorus oxyhalide reagents mentioned above are preferably reacted in an approximate 2:1 molar ratio in the presence of a Lewis acid catalyst, such as aluminum trichloride, magnesium dichloride, titanium tetrachloride, zinc dichloride, and the like. The reaction is advantageously performed at elevated temperature, e.g., about 100° C. to about 220° C., preferably about 120° C. to about 180° C.. The product of the reaction comprises the corresponding compound

where X is halogen, such as chlorine, as a principal component, with evolution of hydrogen halide by-product from the reaction medium. The hindered phenol reagent does not easily substitute all three halogen positions of the starting phosphorus oxytrihalide so that the product formed in this initial step has the desired single halogen functionality for reaction in the next reaction step which is described below. This first step does not result in the production of the undesired amount of oligomers resulting from the first step in the two step processes known to the prior art.

The present invention, unlike the procedure shown in U.S. Pat. No. 3,254,973, relies upon the combining of the reaction product mixture from the first stage of the present process without the isolation of the product

therefrom by distillation.

The reaction product mixture formed in the first stage of the present process is then heated in an approximate molar ratio of reactants of 2:1 with a hydrocarbyl diol of the general formula HO—R—OH, where R can be, for example, a phenyl ring (e.g., hydroquinone or resorcinol), two phenyl rings connected by a bridging group (e.g., bisphenol A, bisphenol S), two phenyl rings directly connected to one another (e.g., 4,4'-diphenol), or an alkylene diol (e.g., neopentyl glycol). Other dihydric compounds comprising the group R can also be selected. The temperatures used can parallel those used in the first step. When the ultimate final product,

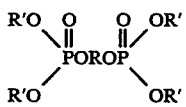

where R and R' are as defined hereinbefore is a solid it can be isolated from the reaction mixture by crystallization from a suitable solvent such as ketones, e.g., methyl isobutyl ketone, alcohols, ethers, or the like. If the product is a liquid it can be washed with an aqueous caustic prior to isolation.

The following Examples further illustrate the invention.

EXAMPLE 1

This illustrates preparation of hydroquinone bis(dixylenyl phosphate).

First, 978.5 g of 2,6-xylenol (8.01 moles), 614 g (4.0 moles) of phosphorus oxychloride, and 13.3 g of aluminum chloride were slowly heated to 150° C. and kept at this temperature for three hours. At the end of this time, hydrogen chloride evolution had subsided. Then, 220.5 g (2.0 moles) of hydroquinone were added to the reaction mixture. The hydrogen chloride temperature was then raised to and kept at 180° C. until evolution ceased.. Methyl isobutyl ketone (1900 ml) was added to the hot reaction mixture with reflux of this ketone occurring. The mixture was allowed to cool slowly with stirring to induce crystallization. A white solid was filtered from the reaction mixture and was rinsed with cold methyl isobutyl ketone. The product was then dried. There was obtained 1194.0 g of a white solid (86.9% yield) melting at 162°-167° C. High pressure liquid chromatography (HPLC) analysis showed 93.9 area % of the desired product.

EXAMPLE 2

This illustrates preparation of resorcinol bis(dixylenyl phosphate).

First, 256.7 g of 2,6-xylenol (2.1 moles), 161.1 g (1.051 moles) of phosphorus oxychloride, and 3.7 g of aluminum chloride were slowly heated to 150° C. and kept at this temperature for three hours. At the end of this time, hydrogen chloride evolution had subsided. Then, 57.8 g (0.525 mole) of resorcinol were added to the reaction mixture. The hydrogen chloride temperature was then raised to and kept at 180° C. until evolution ceased. The reaction mixture was cooled to 120° C., then methanol (500 ml) was added. The mixture was allowed to cool slowly with stirring to induce crystallization. A white solid was filtered from the reaction mixture and was rinsed with cold methanol. The product was then dried. There was obtained 280.1 g of a white solid (78% yield) melting at 77°–79° C. HPLC analysis showed 85.0 area % of the desired product.

COMPARATIVE EXAMPLE 3

This Example illustrates the more complex process for making hydroquinone bis(2,6-xylenylphosphate) by reacting hydroquinone and phosphorus oxytrichloride.

Initially, 55.1 g of hydroquinone (0.50 mole), 306.6 g of phosphorus oxychloride (186.4 ml, 2.0 moles), and 1.0 g of magnesium chloride were slowly heated to 100°–105° C. The reaction mixture was kept in this temperature range for 2.5 hours. Infrared analysis confirmed the first part of the reaction was complete. A white solid material began to precipitate as the temperature was decreased to 59° C. The temperature was then raised. From 75° C. to 111° C., excess phosphorus oxychloride was removed by distillation under reduced pressure. A white paste-like material formed as phosphorus oxychloride was removed. At 111° C., 209.7 g of molten 2,6-xylenol (1.72 moles) were added to the white paste-like material. As the temperature was increased to 150° C., the hydrogen chloride gas evolution rate was rapid. The brown reaction mixture was held at 150° C. for seventeen and one-half hours.

Then, 200 mls of methylene chloride was added slowly to the reaction mixture at 116° C. The mixture was transferred to a one liter vessel and was washed four times with 250 ml of 2% aqueous sodium hydroxide at 30° C. A yellow-brown emulsion resulted from the caustic washes. Saturated sodium chloride aided the layer separations.

Two 250 ml deionized water washes were performed on the emulsified organic phase. The addition of saturated sodium chloride was needed for better layer separation. The layer separations were very slow, therefore the emulsions were allowed to separate overnight. Excess water was then removed from the organic layer using a rotary evaporator. The product that was recovered was 318.2 g of a tan gummy material. HPLC analysis of the material after caustic washing indicated that a major portion of the product were designated P2, P3, and P4, where P2, P3, and P4, respectively, indicate the number of phosphorus atoms in the product. P2 was 49.6 area %, P3 was 9.9 area %, and P4 was 1.7 area %. There was a high level of 2,6-xylenol (19.1 area %) remaining after the caustic washes.

The foregoing Examples should not be construed in a limiting sense since they are intended to merely describe certain embodiments of the invention and are not intended to exemplify the true scope of the invention. The scope of protection sought is set forth in the claims which follow.

We claim:

1. A process for forming a hydrocarbyl bisphosphate compound containing hindered aryl substituents in the phosphate groups which comprises:
   (a) reacting a hindered phenol, containing substitution adjacent the hydroxy group selected from the group consisting of (i) branched lower alkyl when a single substituent is present and (ii) lower alkyl when two substituents are present, with a phosphorus oxytrihalide to form a reaction product mixture; and (b) combining the reaction product from mixture (a), without distillation of product therefrom, with a hydrocarbyl diol to form the hydrocarbyl bisphosphate compound.

2. A process as claimed in claim 1 wherein the hindered phenol is xylenol.

3. A process as claimed in claim 1 wherein the hydrocarbyl diol is hydroquinone.

4. A process as claimed in claim 2 wherein the hydrocarbyl diol is hydroquinone.

5. A process as claimed in claim 1 wherein the hydrocarbyl diol is resorcinol.

6. A process as claimed in claim 2 wherein the hydrocarbyl diol is resorcinol.

* * * * *